(12) United States Patent
Ekman et al.

(10) Patent No.: US 8,808,250 B2
(45) Date of Patent: Aug. 19, 2014

(54) AUTO-INJECTOR WITH A TORSION SPRING

(75) Inventors: Matthew Ekman, Macclesfield (GB); Timothy Donald Barrow-Williams, St. Albans (GB); Yannick Hourmand, Haslingfield (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 71 days.

(21) Appl. No.: 13/579,928

(22) PCT Filed: Feb. 16, 2011

(86) PCT No.: PCT/EP2011/052299
§ 371 (c)(1),
(2), (4) Date: Jan. 22, 2013

(87) PCT Pub. No.: WO2011/101377
PCT Pub. Date: Aug. 25, 2011

(65) Prior Publication Data
US 2013/0123697 A1 May 16, 2013

Related U.S. Application Data

(60) Provisional application No. 61/412,083, filed on Nov. 10, 2010.

(30) Foreign Application Priority Data

Feb. 18, 2010 (EP) ...................................... 10153993

(51) Int. Cl.
| | | |
|---|---|---|
| *A61M 5/32* | (2006.01) | |
| *A61M 5/315* | (2006.01) | |
| *A61M 5/20* | (2006.01) | |

(52) U.S. Cl.
CPC .......... *A61M 5/3232* (2013.01); *A61M 5/31583* (2013.01); *A61M 2005/325* (2013.01); *A61M 5/3202* (2013.01); *A61M 2005/206* (2013.01); *A61M 5/2033* (2013.01); *A61M 2005/2073* (2013.01); *A61M 2005/3152* (2013.01); *A61M 5/326* (2013.01)
USPC ............ 604/195; 604/196; 604/136; 604/187

(58) Field of Classification Search
CPC ................ A61M 5/20; A61M 5/2033; A61M 2005/2026; A61M 2005/206; A61M 2005/2073; A61M 2005/2086
USPC .................. 604/195, 196, 197, 135, 136, 187
See application file for complete search history.

(56) References Cited

U.S. PATENT DOCUMENTS

2008/0051715 A1   2/2008   Young et al.
2010/0280460 A1*  11/2010  Markussen ................... 604/195

FOREIGN PATENT DOCUMENTS

| GB | 2 461 088 A | 12/2009 |
| WO | 2004/047893 A1 | 6/2004 |
| WO | 2009/081133 A1 | 7/2009 |
| WO | 2009/141650 A2 | 11/2009 |

OTHER PUBLICATIONS

International Preliminary Report on Patentability for Int. App. No. PCT/EP2011/052299, mailed Aug. 30, 2012.
International Search Report for Int. App. No. PCT/EP2011/052299, completed Apr. 7, 2011.

* cited by examiner

*Primary Examiner* — Laura Bouchelle
(74) *Attorney, Agent, or Firm* — McDonnell Boehnen Hulbert & Berghoff LLP

(57) ABSTRACT

The invention relates to an auto-injector for administering a dose of a liquid medicament (M), comprising:
- an elongate outer casing arranged to contain a syringe with a hollow needle and a stopper for sealing the syringe and displacing the medicament (M), the outer casing having a distal end (D) and a proximal end (P) with an orifice intended to be applied against an injection site, wherein the syringe is slidably arranged with respect to the outer casing, spring means capable of, upon activation:
- pushing the needle past the proximal end (P),
- operating the syringe to supply the dose of medicament (M), and
- retracting the syringe with the needle activating means arranged to lock the spring means in a pressurized state prior to manual operation and capable of, upon manual operation, releasing the spring means for injection, wherein the spring means is a torsion spring grounded at one end in the outer casing and at the other end in a first gear member rotatable about a longitudinal axis, wherein the first gear member, upon rotation, is arranged for translatively moving a second gear member toward the proximal end (P), the second gear member prevented from rotating and coupled to the stopper in order to push it towards the proximal end (P), wherein the first gear member is engaged with the activating means prior to manual operation in a manner to prevent rotation and disengaged from the activating means upon manual operation.

15 Claims, 7 Drawing Sheets

AUTO-INJECTOR WITH A TORSION SPRING

CROSS REFERENCE TO RELATED APPLICATIONS

The present application is a U.S. National Phase Application pursuant to 35 U.S.C. §371 of International Application No. PCT/EP2011/052299 filed Feb. 16, 2011, which claims priority to U.S. Provisional Patent Application No. 61/412,083 filed on Nov. 10, 2010 and European Patent Application No. 10153993.0 filed Feb. 18, 2010. The entire disclosure contents of these applications are herewith incorporated by reference into the present application.

FIELD OF INVENTION

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

According to the invention, an auto-injector for administering a dose of a liquid medicament comprises:
  an elongate outer casing arranged to contain a syringe with a hollow needle and a stopper for sealing the syringe and displacing the medicament, the outer casing having a distal end and a proximal end with an orifice intended to be applied against an injection site, wherein the syringe is slidably arranged with respect to the outer casing,
  spring means capable of, upon activation:
    pushing the needle from a covered position inside the outer casing into an advanced position through the orifice and past the proximal end,
    operating the syringe to supply the dose of medicament, and
    retracting the syringe with the needle into the covered position after delivering the medicament,
  activating means arranged to lock the spring means in a pressurized state prior to manual operation and capable of, upon manual operation, releasing the spring means for injection.

In the context of this patent application the term proximal refers to the direction pointing towards the patient during an injection while the term distal refers to the opposite direction pointing away from the patient.

According to the invention the spring means is a torsion spring grounded at one end in the outer casing and at the other end in a first gear member rotatable about a longitudinal axis. The first gear member, upon rotation, is arranged for translatively moving a second gear member toward the proximal end. The second gear member is prevented from rotating and coupled to the stopper in order to push it towards the proximal end. The first gear member is engaged with the activating means prior to manual operation in a manner to prevent rotation and disengaged from the activating means upon manual operation.

The single torsion spring is used for inserting the needle, fully emptying the syringe and retracting the syringe and needle to a safe position after injection. A major advantage of the torsion spring is that force is exerted on the stopper and syringe in a smooth manner, whereas a conventional compression spring exhibits a rather abrupt force deployment which may spoil a glass syringe or other parts of the auto-injector.

The first and second gear members may be in the shape of tubes telescoped into each other. The first gear member may be a cam follower tube and the second gear member a lead screw tube, with the lead screw tube telescoped into the cam follower tube. The lead screw tube has a lead screw thread engaged with the cam follower tube by at least one ball bearing. In an alternative embodiment the cam follower tube may be engaged with the lead screw by a pin. However, the ball bearing is preferred in order to achieve a low friction contact.

The syringe may be held in an essentially tubular syringe carrier and supported at its proximal end therein, wherein the syringe carrier is slidably arranged in the lead screw tube. Supporting the syringe at its proximal end rather than at its flanges avoids damaging the syringe under load since the flanges are more fragile, in particular in a glass syringe.

In a preferred embodiment the first gear member is coupled to a retraction slider tube for joint translative movement but independent rotation. The retraction slider tube is arranged in a proximal part of the outer casing in a manner to be prevented from rotation, e.g. by one or more flats or splines guided in correspondent flats or splines in the outer casing. Furthermore latches for preventing the retraction slider tube from being axially moved are provided in the outer casing. The latches are engaged for the most part of the operation of the auto-injector, i.e. before and during needle insertion and injection. When the second gear member is advanced into or near a maximum proximal position at the end of the injection the latches are disengaged by ramp features of the second gear member pushing the latches outward thus releasing the retraction slider tube for being translatively moved in distal direction. As long as the latches are engaged the second gear member is forced in proximal direction by the axially fixed and rotating first gear member. When the latches are disengaged the second gear member has at least nearly reached the end of its travel and bottomed out at the proximal end of the outer casing. Due to the disengaged latches the first gear member and the retraction slider tube are now pulled in distal direction by continued rotation of the torsion spring and the first gear member since the second gear member cannot advance further. The retraction slider tube comprises at least one dog feature for taking along the syringe carrier with the syringe when the retraction slider tube is retracted. The syringe carrier is retracted into the auto-injector until the hollow needle is fully covered. The dog feature preferably extends inwardly from the retraction slider tube through recesses in the lead screw tube.

In order to insert the hollow needle and to inject the dose the second gear member may be coupled to the stopper by a plunger which is releasably engageable with the second gear member for joint axial movement. The plunger is disengageable from the second gear member upon the second gear member reaching its maximum proximal position in order to allow the syringe to be retracted after injection.

In a preferred embodiment the plunger is engageable with the second gear member by at least one plunger ball detent. The detent ball may be held in a recess in the second gear member and engage a circumferential notch in the plunger. In order to stay engaged with the notch the ball is supported by the first gear member until the second gear member reaches the end of its travel. At this point the detent ball reaches a pocket in the first gear member so it is no longer supported and the detent ball drops into the pocket thus disengaging the plunger from the second gear member.

Preferably the plunger comprises a plunger rear and a plunger front telescoped into each other. A plunger spring is arranged between the plunger rear and plunger front. The plunger spring may be a compression spring or a piece of foam or a pneumatic spring. It is arranged for being partially compressed when the plunger is advanced to push the stopper towards the proximal end. This partial compression happens due to friction between the stopper and the inner wall of the syringe and due to hydraulic resistance of the liquid medicament forced through the small fluid channel in the hollow needle.

The second gear member may be provided with pockets containing a respective viscous damper at the proximal end of the second gear member. The viscous damper is arranged for being compressed by a respective rib arranged in the proximal end of the outer casing when the second gear member nearly reaches its maximum proximal position. Thereby part of the load from the second gear member is resolved and the plunger spring is allowed to expand. Thus the stopper is advanced further by the compression spring so residual medicament is expelled from the syringe. This allows for dealing with the problem that the syringe and stopper are subject to large tolerances making it virtually impossible to expel the whole content of the syringe and trigger the retraction of the syringe exactly at the end of the injection. With conventional auto-injectors the stopper will either bottom out before the retraction can be triggered. Thus the syringe is emptied but the syringe and needle are never retracted so the risk for needle-stick injuries is tremendously increased. Or the retraction will be triggered before the stopper bottoms out in the syringe. In this case the syringe and needle are indeed retracted to a safe position but the syringe is not fully emptied.

The auto-injector with the viscous damper and the plunger spring allows for solving both problems, reliably retracting the hollow needle to a safe position and fully emptying the syringe which is particularly desirable with expensive drugs. Emptying the syringe is also important for dosage accuracy.

When the stopper has nearly reached the end of its travel the viscous damper contacts ribs in the proximal end of the outer casing. A velocity dependent load opposes the motion of the second gear member slowing it down. As a result load on the plunger is reduced. This allows the plunger spring to expand and empty the residual dose of medicament. The second gear member is further advanced until it bottoms out in the proximal end of the outer casing. Shortly before this the ramp features disengage the latches so the retraction slider tube can be moved in the distal direction taking with it the syringe carrier and syringe as soon as the plunger and the second gear member are decoupled by the detent ball falling into the pocket. Thus the stopper is kept from stalling the retraction and the syringe is fully emptied.

The first gear member and the retraction slider tube preferably exhibit respective circumferential shoulders facing each other and held together by a coupling ring. This allows for independent rotation while joint axial movement is ensured.

In a preferred embodiment the lead screw thread has a variable pitch arranged in a manner to advance the second gear member faster and with less force when inserting the hollow needle (steep pitch) and more slowly with increased force when expelling the medicament (flat pitch). At the end of the travel of the second gear member the pitch is preferably even flatter in order to increase the force for compressing the viscous damper. A rapid needle insertion is known to reduce pain felt by the patient. A variable pitch also allows a steady delivery of the dose. The repeatability of the time required for the operational cycle of the auto-injector is important to the user. If the time required is highly variable between devices then the user may be confused and make errors in delivering the injection. Changing the pressure angle of the lead screw or cam track allows the load from the spring to be applied either more or less directly to the plunger, e.g. if there is a step in the device cycle that requires a high axial load such as when compressing the viscous damper or operating the latches for triggering the needle retraction.

The activating means may be a trigger button arranged at the distal end of the outer casing and operable by being pressed in proximal direction.

In a preferred embodiment the trigger button is splined to the outer casing for preventing relative rotation. The trigger button may be engageable to the distal end of the first gear member by longitudinal splines engaged in an initial state for preventing relative rotation and disengageable by pushing the trigger button in proximal direction. Thus when the splines are engaged, but with the trigger button not pressed, the load of the torsion spring is statically resolved in the outer casing so the first gear member cannot rotate. When the trigger button is pressed the splines are disengaged and the first gear member starts rotating driven by the torsion spring.

A locking collar may be arranged at the distal end of the outer casing, wherein the locking collar is rotatable between a locked position and an unlocked position. In the locked position the trigger button is prevented from proximal movement and in the unlocked position the trigger button may be pressed allowing proximal movement and operation of the device. Thus the auto-injector is prevented from being unintentionally triggered.

Usually the hollow needle is equipped with a protective needle shield for keeping the needle sterile and preventing it from being mechanically damaged. The protective needle shield is attached to the needle when the auto-injector or the syringe is assembled.

In a preferred embodiment of the invention a finger guard is provided in the outer casing at the proximal end. The finger guard comprises a spring with two inwardly biased spring arms arranged for bearing against the protective needle shield. Furthermore the sheet metal spring has a respective locking arm assigned to each spring arm which is biased in distal direction and thus bearing against the respective spring arm when the protective needle shield is in place. The spring arms are arranged to move inwards when the protective needle shield is removed thus allowing the locking arms to move distally into a position where they prevent the spring arms from being pushed outward again.

The spring of the finger guard may be a sheet metal, wire or plastic spring.

Conventional auto-injectors achieve needle safety by starting with the needle held some distance back within the body of the device. Upon actuation the needle moves forward by a distance that is the sum of the hiding distance and the required injection depth. By using the aforementioned finger guard with the sheet metal spring the hiding distance may be safely reduced. Thus the auto-injector may be made shorter, more portable and attractive to users.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

An alternative embodiment of the auto-injector may be arranged to swap the end of the torsion spring grounded to the outer casing to reverse the direction of rotation in order to first advance the syringe with the needle and inject the dose and then retract the needle with reversed sense of rotation. Thus the overall length of the auto-injector may be further reduced.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION

Figure 1A:
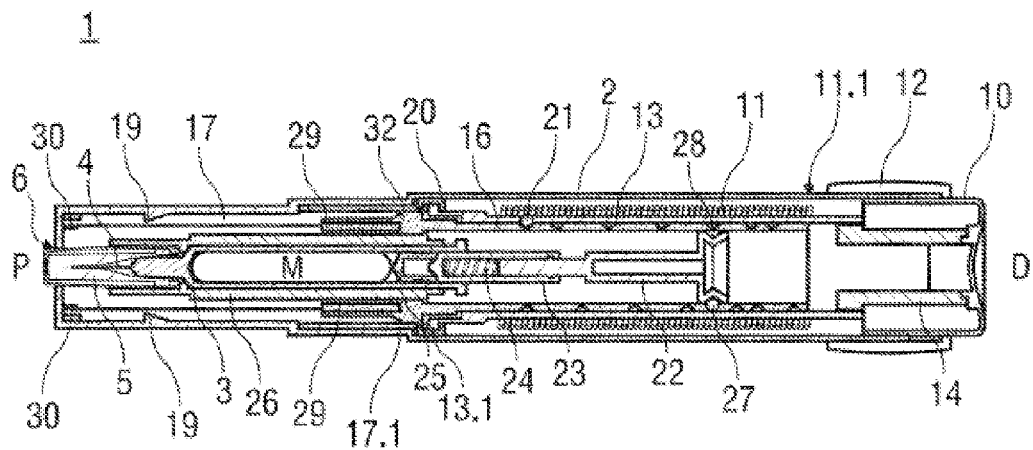
FIG. 1A is a cross-sectional longitudinal view in one plane of an auto-injector with a syringe, a hollow needle and a single torsion spring prior to use.
Figure 1B:
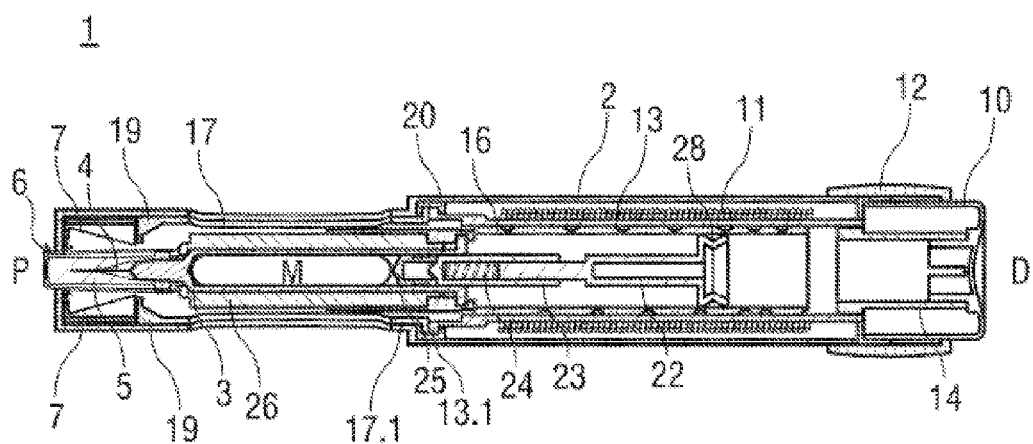
FIG. 1B is a cross-sectional longitudinal view of the auto-injector of FIG. 1A in plane rotated 90 degrees.
Figure 2:
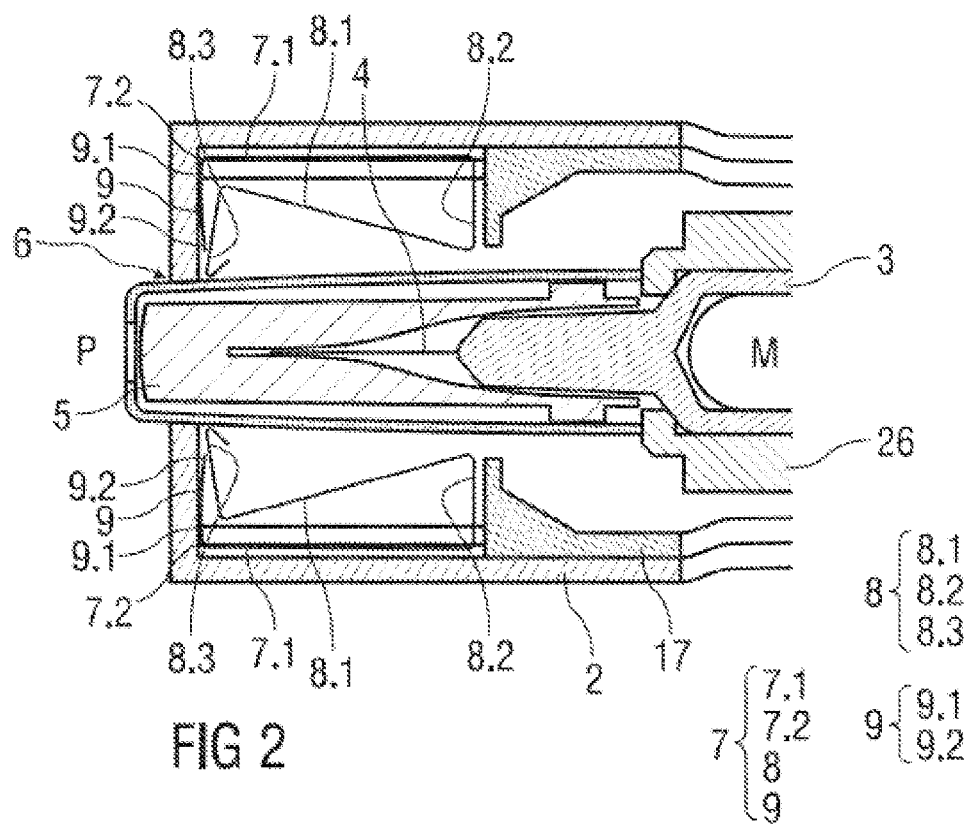
FIG. 2 is a detail view of a finger guard prior to use.
Figure 3:
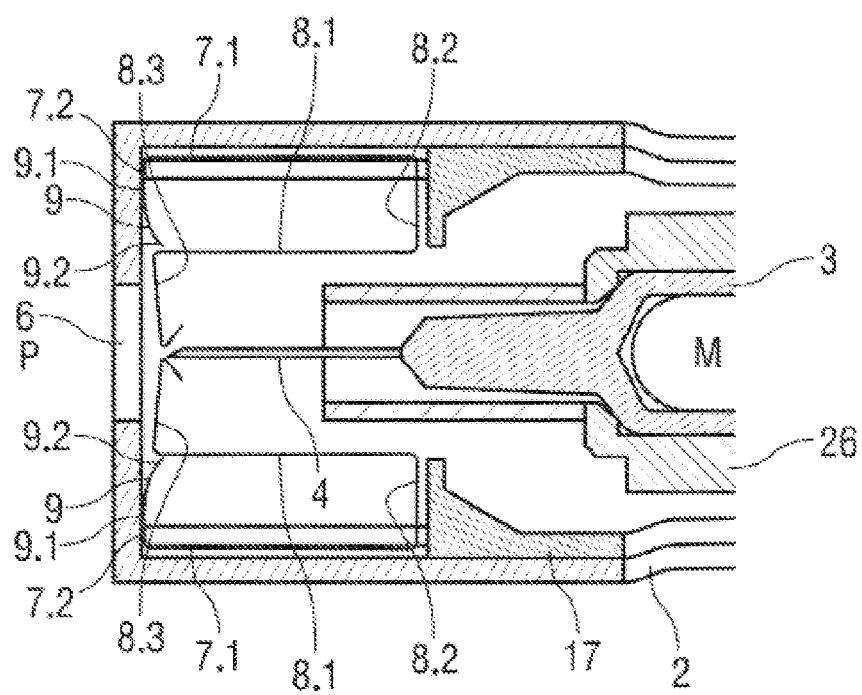
FIG. 3 is a detail view of the finger guard after removal of a rigid needle shield.

FIG. 1 shows two longitudinal sections in different section planes of an auto-injector 1, the different section planes approximately 90° rotated to each other. The auto-injector comprises an elongate outer casing 2. A syringe 3 with a hollow needle 4 is arranged in a proximal part of the auto-injector 1. When the auto-injector 1 is assembled a protective needle shield 5 is attached to the needle 4 and protruding through an orifice 6 at the proximal end P. A finger guard 7 in the shape of a sheet metal spring is arranged near the protective needle shield 5. The finger guard 7 is shown in detail in FIG. 2. The finger guard 7 comprises two spring arms 8 which are inwardly biased so they bear against the protective needle shield 5 as long as it is still in place. A respective locking arm 9 is assigned to each spring arm 8. The locking arms 9 are biased in distal direction D so they bear against a part of the spring arms 8 when the protective needle shield 5 is in place. As the protective needle shield 5 is pulled away from the needle 4 (see FIG. 3) the spring arms 8 move inwards and relax leaving a small gap between them just wide enough to let the needle pass without touching it. This allows the locking arms 9 to come clear of the spring arms 8 and move distally into a position where they prevent the spring arms 8 from being pushed outward again so despite the rather big orifice 6 the user cannot touch the tip of the needle 4. The tips of the spring arms 8 where the spring arms 8 bear against the protective needle shield 5 are rounded off in order to facilitate removal of the protective needle shield 5.

Figures 4A, 4B:
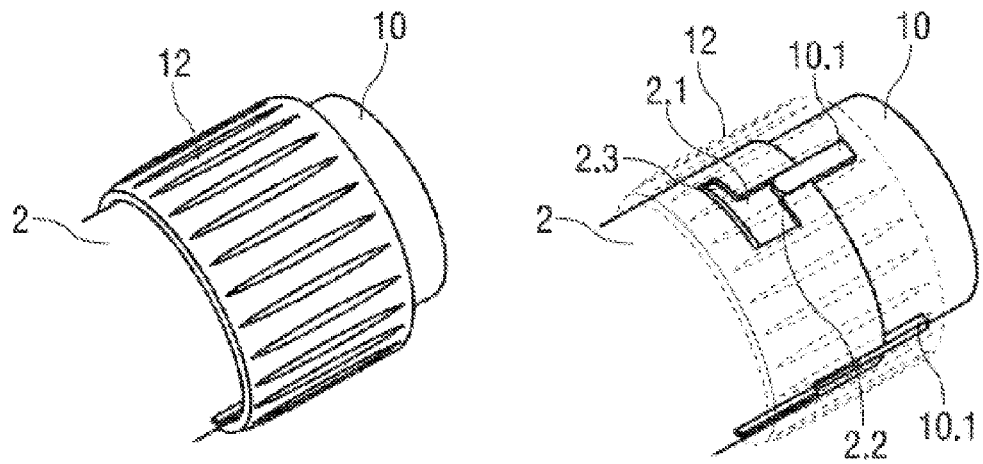
FIG. 4A is a perspective view of one embodiment of a trigger button and a button lock collar.
FIG. 4B is a perspective view of a trigger button spline relative to the outer casing prior to unlocking.

At the distal end D of the auto-injector 1 a trigger button 10 for releasing a torsion spring 11 is arranged. The trigger button 10 may be locked or unlocked by a locking collar 12 which is also arranged at the distal end D (see FIG. 4 for details). The trigger button 10 is equipped with a number of longitudinal splines 10.1 that engage with respective slots 2.1 in the outer casing 2 so the trigger button 10 is prevented from rotating with respect to the outer casing 2 while allowed to be pushed into the outer casing 2 by a certain distance. At least one of the slots 2.1 has a lateral clearance 2.2. The locking collar 12 has an internal protrusion 12.1 (see FIG. 4e) also engaged in the slot 2.1. A small pin 12.2 provided in the collar 12 engages in a guiding clearance 2.3 of the slot 2.1 in order to prevent axial movement of the collar 12. In FIG. 4b the protrusion 12.1 is aligned with one of the splines 10.1 thus preventing the trigger button 10 from being pushed.

The user removes the protective needle shield 5 from the needle 4. For this purpose a device cap (not shown) may be attached to the protective needle shield 5. When the needles shield 5 is removed the finger guard 7 locks into place to protect the user from accidental needlestick injuries.

In order to unlock the trigger button 10 the locking collar 12 is rotated.

Figures 4C, 4D:
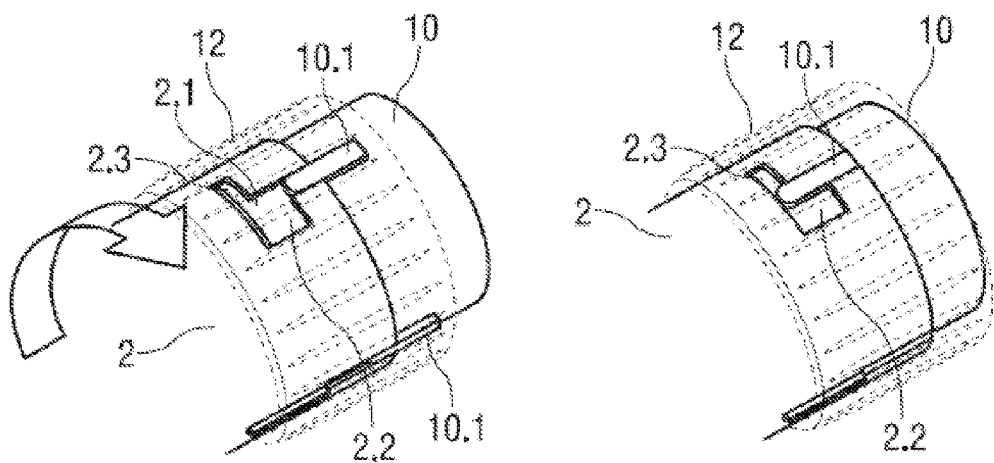
FIG. 4C is a perspective view of the rotation of the locking collar during unlocking of the trigger button.
FIG. 4D is a perspective view of the depression of the trigger button relative to the outer housing after unlocking.
Figure 4E:
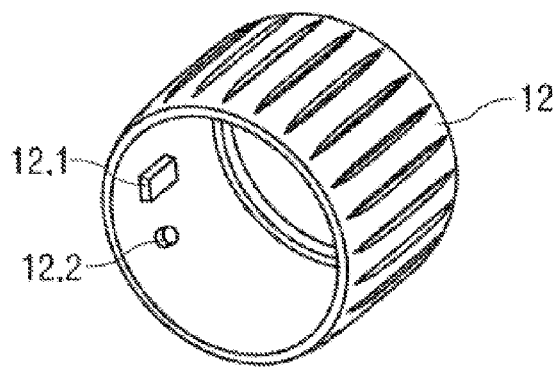
FIG. 4E is a perspective view of the inside surface of the unlocking collar.

In preparation of an injection the user rotates the locking collar 12 by a small angle in the direction indicated by the arrow in FIG. 4c. Thus the protrusion 12.1 is turned out of the alignment with the spline 10.1 and into the clearance 2.2. The trigger button 10 can now be depressed (see FIG. 4d).

The auto-injector 1 is usually shipped with the trigger button 10 in the locked position.

Figure 5A:
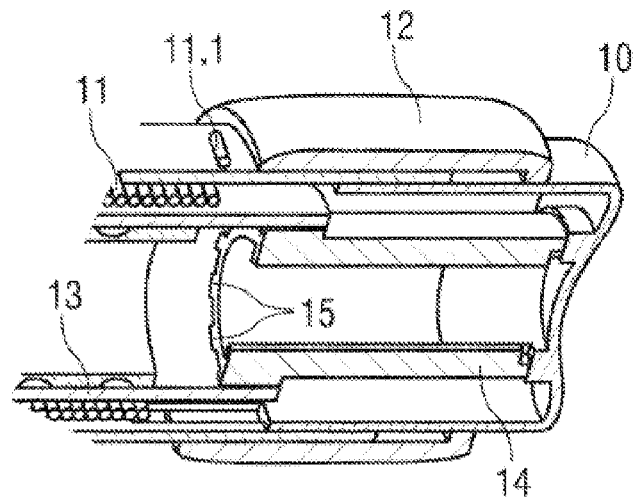
FIG. 5A is a detailed cross-sectional longitudinal view of the trigger button extended.
Figure 5B:
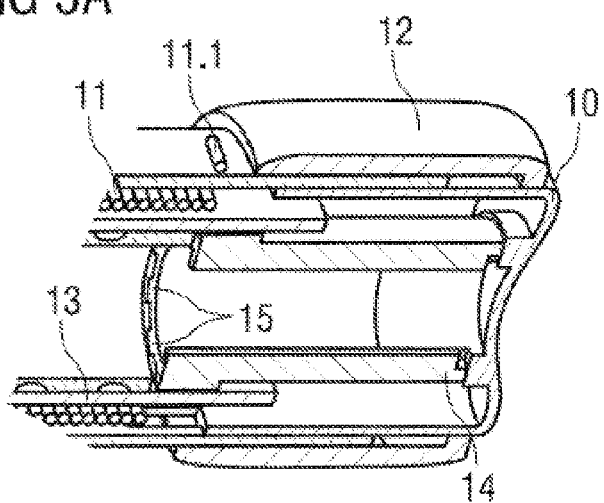
FIG. 5B is a detailed cross-sectional longitudinal view of the trigger button depressed.
Figure 5C:
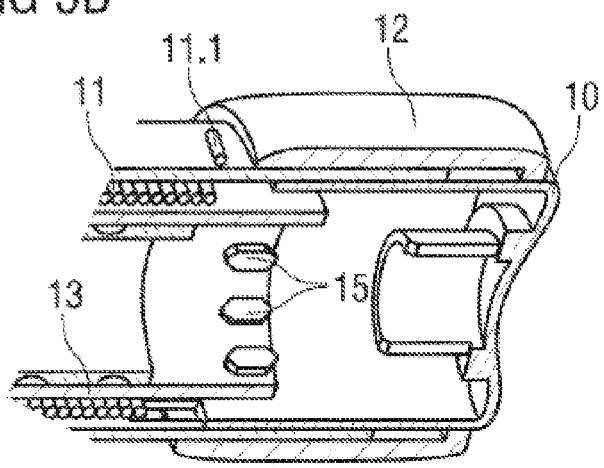
FIG. 5C is a detailed cross-sectional longitudinal view showing the longitudinal splines of the cam follower tube when the coupling member is removed.
Figure 6:
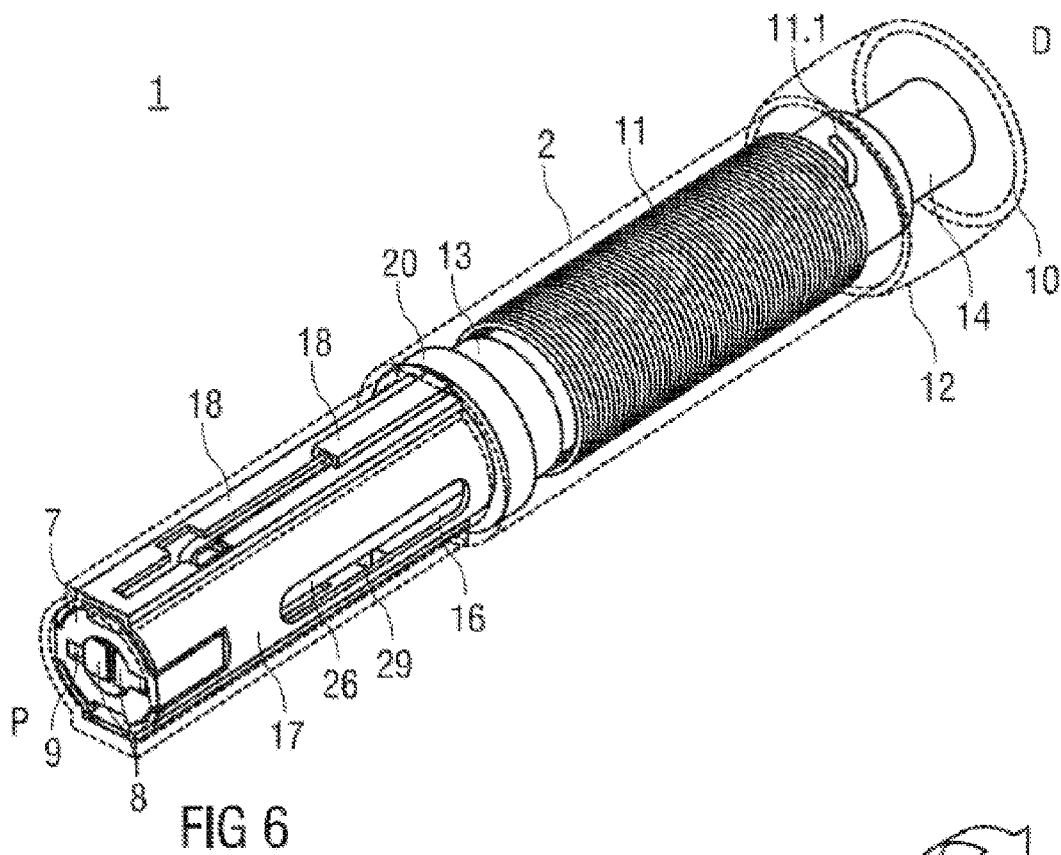
FIG. 6 is a perspective view of the auto-injector with the outer casing removed.
Figure 7:
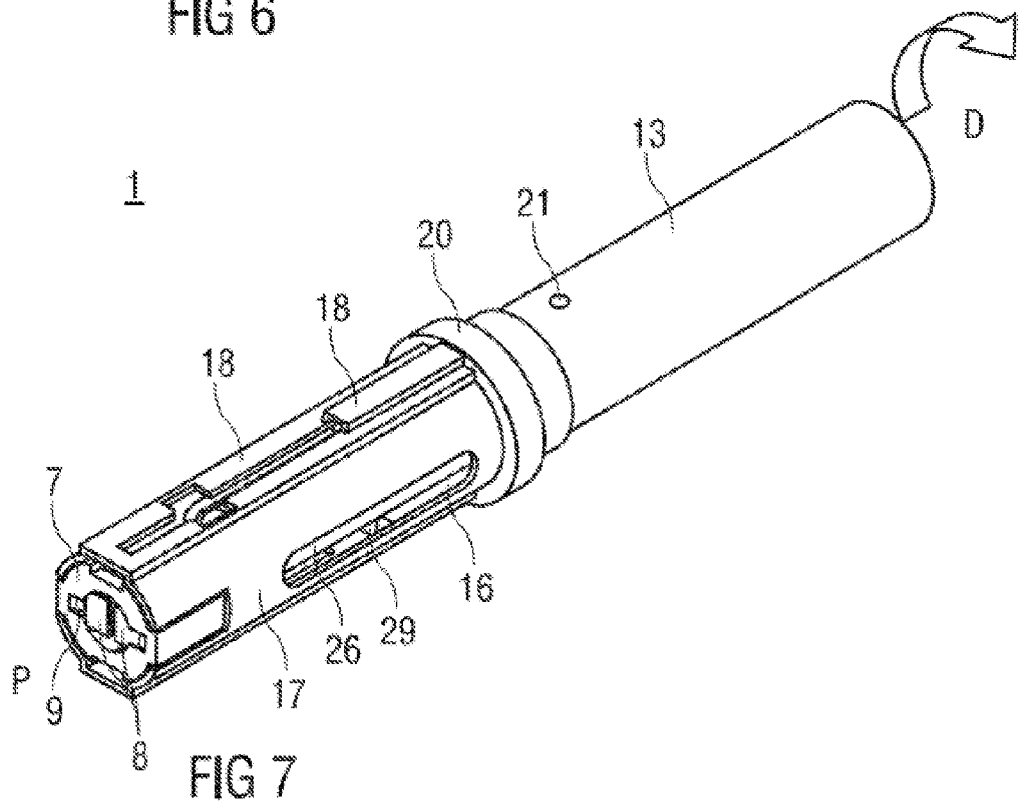
FIG. 7 is a perspective view of the auto-injector with the outer casing and torsion spring removed.
Figure 8:
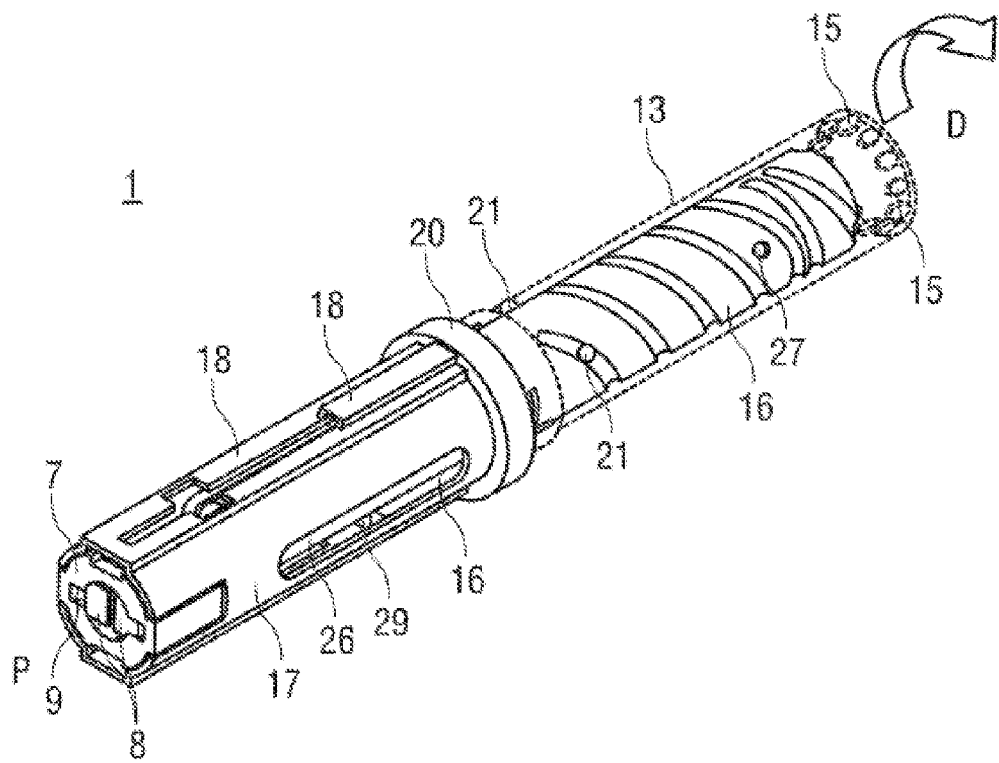
FIG. 8 is a perspective view of the auto-injector with the outer casing, torsion spring and cam follower tube removed.

The torsion spring 11 is arranged inside the outer casing 2 and grounded with its distal end 11.1 in the outer casing 2 near the distal end D of the auto-injector 1 (cf. FIG. 5). The proximal end 11.2 of the torsion spring 11 is grounded in a cam follower tube 13 arranged inside the torsion spring 11 and rotatable with respect to the outer casing 2. Near the distal end D of the auto-injector 1 the cam follower tube 13 is engaged with an essentially tubular coupling member 14 telescoped into the cam follower tube 13. FIG. 5 shows the coupling member 14 in more detail. The distal end of the cam follower tube 13 and the coupling member 14 are provided with respective longitudinal splines 15 which are engaged with each other when the trigger button 10 is not pressed (cf. FIG. 5a). The trigger button 10 is splined to the outer casing 2 (cf. FIG. 4) so the load of the torsion spring 11 is resolved statically. The trigger button 10 is attached to the coupling member 14 in a manner to prevent relative rotation. Alternatively the trigger button 10 and the coupling member 14 may be a one-piece component.

Furthermore, the cam follower tube 13 is telescoped with a lead screw tube 16. The lead screw tube 16 is supported and guided in a retraction slider tube 17 arranged in the proximal part of the outer casing 2 in a manner to prevent the lead screw tube 16 from rotating while allowing it to be moved axially in proximal direction P. The retraction slider tube 17 in turn is engaged with the outer casing 2 by flats 18 and latches 19 in a manner to prevent both rotation and translation with respect to the outer casing 2 at least in the initial situation shown in FIG. 1. It will be shown in the following how the retraction slider tube 17 is disengaged from the latches 19 for being axially moved. The retraction slider tube 17 and the cam follower tube 13 are provided with respective shoulders 17.1, 13.1 held together by a coupling ring 20 for allowing relative rotation but preventing them from being independently axially moved. The lead screw tube 16 has an external lead screw which is engaged with the cam follower tube by a number of ball bearings 21. Rotation of the cam follower tube 13 therefore results in translative movement of the lead screw tube 16.

In the initial situation shown in FIG. 1 the retraction slider tube 17 can neither rotate nor move axially, the cam follower tube 13 cannot move axially and is prevented from rotating by the spline engagement with the coupling member 14 and the lead screw tube 16 is prevented from rotation.

In order to start an injection the user places the auto-injector 1 with the orifice 6 ahead on the injection site and depresses the trigger button 10. When the trigger button 10 is pressed the coupling member 14 is pushed further into the cam follower tube 13 so the splines 15 of the coupling member and the cam follower tube 13 come clear of each other. This allows the cam follower tube 13 to rotate due to the torque of the torsion spring 11. This rotation causes translative movement of the lead screw tube 16 in proximal direction P. Inside the lead screw tube 16 a two part plunger with a plunger rear 22 and a plunger front 23 is arranged, the plunger rear 22 telescoped into the hollow plunger front 23. In the plunger front 23 a plunger spring 24 in the shape of a compression spring is arranged which bears against the plunger rear 22 when the plunger rear 22 pushed in proximal direction P. The plunger front 23 in turn pushes against a stopper 25 arranged for sealing the syringe 3 distally and for displacing a liquid medicament M through the hollow needle 4. The syringe is held in a tubular syringe carrier 26 and supported at its proximal end therein. The plunger rear 22 is coupled for joined axial movement to the lead screw tube 16 by a plunger ball 27 arranged in a recess in the lead screw tube 16 and guided in a circumferential notch 28 of the plunger rear 22. In the initial position shown in FIG. 1 the plunger ball 27 is held in position by the cam follower tube 13 in order to keep the plunger rear 22 and lead screw tube 16 from disengaging.

Consequently, when the lead screw tube 16 is advanced in proximal direction P the syringe 3 is driven forward by the plunger pushing on the stopper 25.

Figure 9:
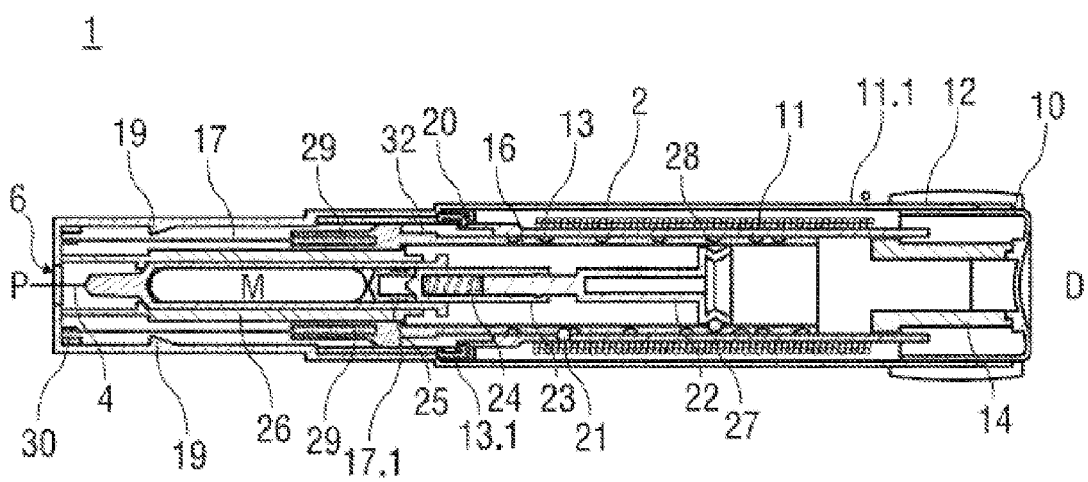
FIG. 9 is the auto-injector with the syringe and needle advanced.

The external lead screw of the lead screw tube 16 has a variable pitch. In the embodiment shown in the figures the pitch is steeper in the proximal part of the external lead screw (cf. FIG. 1). This allows for a rapid insertion of the hollow needle 4 into the patient's skin in order to avoid unnecessary pain for the patient. The load required to insert a siliconized fine gauge needle is thought to be in the region of 5 N, which is relatively low so a steep screw pitch can be used with little risk of the screw engagement locking. FIG. 9 shows the auto-injector with the hollow needle 4 fully advanced.

In case the screw engagement between the cam follower tube 13 and the lead screw tube 16 comprises more than one ball bearing 21 each ball 21 may be held in a respective longitudinal slot hole. Alternatively each ball 21 may be engaged with a respective screw thread so the lead screw tube 16 would have a multi-start thread.

The syringe carrier 26 has bottomed out at the proximal end P of the outer casing 2 thus defining an injection depth, e.g. for a subcutaneous injection.

As the torsion spring 11 continues rotating the lead screw tube 16, and plunger rear 22 are further forwarded. Due to friction effective between the stopper 25 and the inner wall of the syringe 3 and due to the thin fluid channel inside the hollow needle 4 opposing the displacement of the medicament M the stopper 25 exerts a load against the forward movement of the plunger front 23. Thus, the plunger spring 24 is slightly compressed.

The thrust load is reacted through the coupling ring 20 into the retraction slider tube 17 which is coupled to the outer casing 2 by the latches 19. Thus the cam follower tube 13 is kept from moving in distal direction D. With continued forward movement of the plunger the stopper 25 is advanced and injects the medicament M from the syringe 3 into the injection site. During injection of the dose of medicament M the pitch of the lead screw is slightly reduced compared to the needle insertion in order to give a greater mechanical advantage to the lead screw engagement and avoid it stalling due to the increased load.

Figure 10:
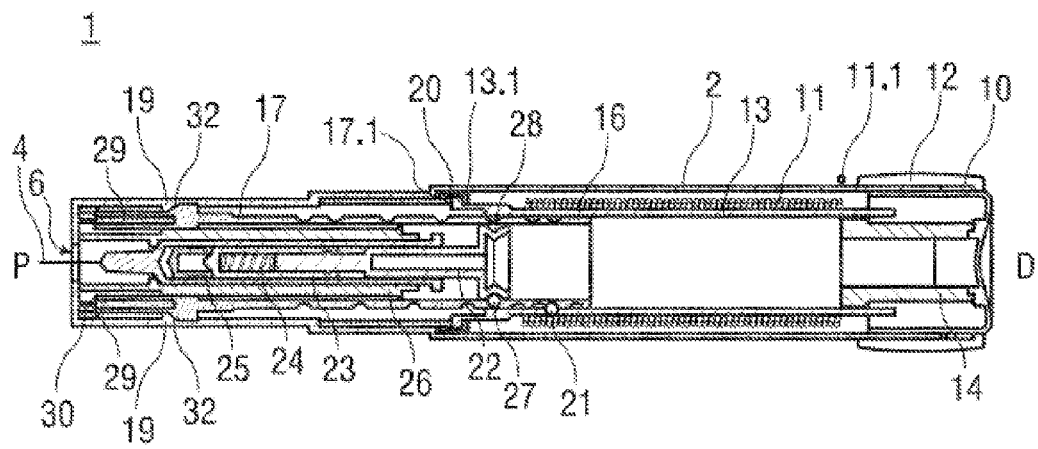
FIG. 10 is the auto-injector near the end of an injection stroke.

In FIG. 10 the auto-injector 1 is shown towards the end of the dose, i.e. just before the stopper 25 bottoms out in the syringe 3. In this situation viscous dampers 29 contained in pockets in the proximal end of the lead screw tube 16 contact small ribs 30 in the proximal end P of the outer casing 2. Thus load from the torsion spring 11 is shared between the stopper 25 and the contact between the ribs 30 and the viscous dampers 29, so the plunger spring 24 is allowed to extend and complete the dose by fully advancing the stopper 25. This allows for fully emptying the syringe 3 before starting to retract the needle 4.

The viscous damper 29 has a speed dependent load characteristic. In this instance the load from the torsion spring 11 is almost constant over the small axial travel of the viscous damper 29 so the speed can be tuned so that the plunger spring 24 has enough time to fully expel the residual contents of the syringe 3. The material of the viscous damper 29 may be viscoelastic foam or a fluid forced through a small orifice.

A change in the lead screw pitch at this point allows a controlled increase in the mechanical advantage to apply sufficient force to the mechanism.

Figure 11:
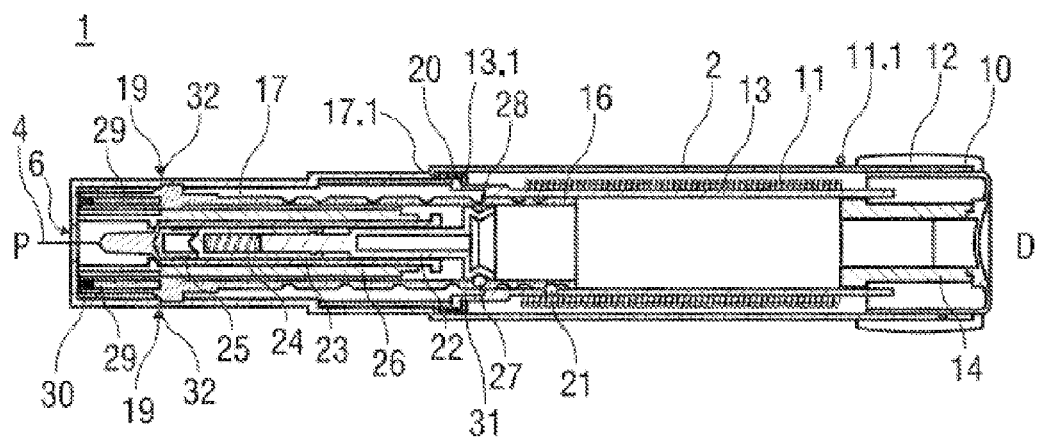
FIG. 11 is the auto-injector at the end of the injection stroke.
Figure 12:
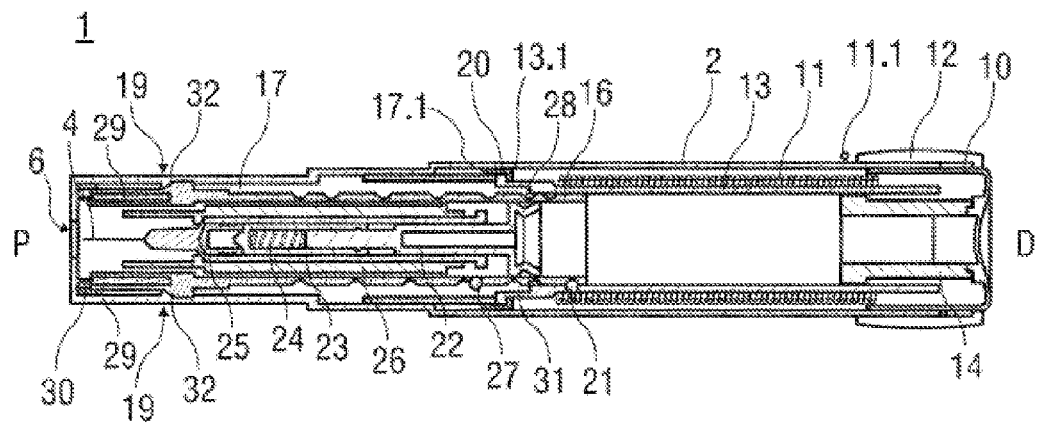
FIG. 12 is the auto-injector after the end of the injection with the needle retracted into the housing.

In FIG. 11 the stopper 25 has bottomed out in the syringe and the lead screw tube 16 reaches the end of travel. The plunger ball 27 disengages the plunger rear 22 from the lead screw tube 16 by dropping out of its recess into a pocket 31 in the cam follower tube 13. Just after this the latches 19 are released by ramp features 32 of the lead screw tube 16 pushing them outward so the retraction slider tube 17 and the cam follower tube 13 are released from the outer casing 2 with respect to translative movement. Since the lead screw tube 16 has bottomed out at the proximal end P of the outer casing continued rotation of the torsion spring results in a backward movement of the retraction slider tube 17 and the cam follower tube 13 which is still rotating. The retraction slider tube 17 takes along the syringe carrier 26 and retracts it into the auto-injector 1 until the hollow needle 4 is fully covered. For this purpose the retraction slider tube 17 may have one or more dog features extending inwardly through recesses in the lead screw tube 16 and engaging the syringe carrier 26 (dog features not illustrated).

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. Auto-injector for administering a dose of a liquid medicament (M), comprising:
    an elongate outer casing arranged to contain a syringe with a hollow needle and a stopper for sealing the syringe and displacing the medicament (M), the outer casing having a distal end (D) and a proximal end (P) with an orifice intended to be applied against an injection site, wherein the syringe is slidably arranged with respect to the outer casing,
    a spring capable of, upon activation:
    pushing the needle from a covered position inside the outer casing into an advanced position through the orifice and past the proximal end (P),
    operating the syringe to supply the dose of medicament (M), and
    retracting the syringe with the needle into the covered position after delivering the medicament (M),
    an activation mechanism arranged to lock the spring in a pressurized state prior to manual operation and capable of, upon manual operation, releasing the spring for injection,
    a first gear member rotatable relative to the outer casing,
    a second gear member non-rotatable relative to first member and the outer casing and threadedly engaged with the first gear member,
    characterized in that the spring is a torsion spring grounded at one end in the outer casing and at the other end in a first gear member rotatable about a longitudinal axis, wherein the first gear member, upon rotation, is arranged for translatively moving a second gear member toward the proximal end (P), the second gear member prevented from rotating and coupled to the stopper in order to push it towards the proximal end (P), wherein the first gear member is engaged with the activation mechanism prior to manual operation in a manner to prevent rotation and disengaged from the activation mechanism upon manual operation.

2. Auto-injector according to claim 1, characterized in that the first gear member is a cam follower tube and that the second gear member is a lead screw tube, wherein the lead screw tube is telescoped into the cam follower tube, wherein the lead screw tube has a lead screw thread engaged with the cam follower tube by at least one ball bearing.

3. Auto-injector according to claim 2, characterized in that the syringe is held in an essentially tubular syringe carrier and supported at its proximal end therein, wherein the syringe carrier is slidably arranged in the lead screw tube.

4. Auto-injector according to claim 3, characterized in that the first gear member is coupled to a retraction slider tube for joint translative movement but independent rotation, wherein the retraction slider tube is arranged in a distal part of the outer casing in a manner to be prevented from rotation and wherein latches for preventing the retraction slider tube from being axially moved are provided in the outer casing, the latches being disengageable by ramp features of the second gear member when the second gear member is in or near a maximum proximal position, wherein the retraction slider tube comprises at least one dog feature for taking along the syringe carrier with the syringe when the retraction slider tube is retracted.

5. Auto-injector according to claim 4, characterized in that the retraction slider tube is retractable by the first gear member when the second gear member has bottomed out in the outer casing when in its maximum proximal position, wherein the latches are released by the ramp features.

6. Auto-injector according to claim 4, characterized in that the first gear member and the retraction slider tube exhibit respective shoulders facing each other and held together by a coupling ring.

7. Auto-injector according to claim 2, characterized in that the lead screw thread has a variable pitch arranged in a manner to advance the second gear member faster and with less force when inserting the hollow needle and more slowly with increased force when expelling the medicament (M).

8. Auto-injector according to claim 1, characterized in that the second gear member is coupled to the stopper by a plunger which is releasably engageable with the second gear member for joint axial movement, wherein the plunger is disengageable from the second gear member upon the second gear member reaching its maximum proximal position.

9. Auto-injector according to claim 8, characterized in that the plunger is engageable with the second gear member by at least one plunger ball detent, wherein the ball detent is supported by the first gear member when engaged and wherein the plunger is disengageable by the ball detent reaching a pocket in the first gear member and the detent ball dropping into the pocket.

10. Auto-injector according to claim 8, characterized in that the plunger comprises a plunger rear and a plunger front telescoped into each other, wherein a plunger spring is arranged between the plunger rear and plunger front, wherein the plunger spring is arranged for being partially compressed when the plunger is advanced to push the stopper towards the proximal end (P).

11. Auto-injector according to claim 10, characterized in that the second gear member is provided with pockets containing a respective viscous damper at the proximal end of the second gear member the viscous damper arranged for being compressed by a respective rib arranged in the proximal end of the outer casing when the second gear member nearly reaches a maximum proximal position thereby resolving part of the load from the second gear member and allowing the plunger spring to expand.

12. Auto-injector according to claim 1, characterized in that the activating means is a trigger button, arranged at the distal end of the outer casing and operable by being pressed in proximal direction (P).

13. Auto-injector according to claim 12, characterized in that the trigger button is splined to the outer casing for preventing relative rotation and engageable to the distal end of the first gear member by longitudinal splines engaged in an initial state for preventing relative rotation and disengageable by pushing the trigger button in proximal direction (P).

14. Auto-injector according to claim 12, characterized in that a locking collar is arranged at the distal end (D) of the outer casing, the locking collar rotatable between a locked position and an unlocked position, wherein the trigger button is prevented from being pressed in the locked position and released for being pressed in the unlocked position.

15. Auto-injector according to claim 1, characterized in that a finger guard is provided in the outer casing at the proximal end (P), the finger guard comprising a sheet metal spring with two inwardly biased spring arms arranged for bearing against a protective needle shield arranged at the hollow needle, the sheet metal spring further having a respective locking arm assigned to each spring arm biased in distal direction (D) thus bearing against the respective spring arm when the protective needle shield is in place, wherein the spring arms are arranged to move inwards when the protective needle shield is removed thus allowing the locking arms to move distally into a position where they prevent the spring arms from being pushed outward again.

\* \* \* \* \*